(12) United States Patent
Daas et al.

(10) Patent No.: US 11,000,284 B2
(45) Date of Patent: May 11, 2021

(54) DEVICE FOR COMMUNICABLY COUPLING A FIRST AND A SECOND ORGAN BODY

(71) Applicant: LYDUS MEDICAL LTD., Tel Aviv (IL)

(72) Inventors: Kamal Daas, Tira (IL); Dean Ad-El, Mazor (IL); Muhammad Azmi Mansour, Tira (IL)

(73) Assignee: LYDUS MEDICAL LTD.

( * ) Notice: Subject to any disclaimer, the term of this patent is extended or adjusted under 35 U.S.C. 154(b) by 125 days.

(21) Appl. No.: 15/549,254

(22) PCT Filed: Jan. 25, 2016

(86) PCT No.: PCT/IL2016/050078
§ 371 (c)(1),
(2) Date: Aug. 7, 2017

(87) PCT Pub. No.: WO2016/128961
PCT Pub. Date: Aug. 18, 2016

(65) Prior Publication Data
US 2018/0199943 A1   Jul. 19, 2018

(30) Foreign Application Priority Data

Feb. 10, 2015 (DE) ............. 10 2015 001 656.3
Feb. 13, 2015 (DE) ............. 10 2015 001 781.0
(Continued)

(51) Int. Cl.
*A61B 17/11* (2006.01)
*A61B 17/06* (2006.01)
(Continued)

(52) U.S. Cl.
CPC ...... *A61B 17/1128* (2013.01); *A61B 17/0482* (2013.01); *A61B 17/06066* (2013.01);
(Continued)

(58) Field of Classification Search
CPC ............. A61B 17/11; A61B 17/06128; A61B 17/06123; A61B 17/06119;
(Continued)

(56) References Cited

U.S. PATENT DOCUMENTS 1,449,068 A * 3/1923 Snyder ............. A61B 17/06004
606/225
4,524,771 A * 6/1985 McGregor ....... A61B 17/06066
223/102
(Continued)

FOREIGN PATENT DOCUMENTS

WO        8503858        9/1985

OTHER PUBLICATIONS

International Search Report of PCT/IL2016/050078 Completed Sep. 20, 2016; dated Dec. 16, 2016 4 pages.
(Continued)

*Primary Examiner* — Tuan V Nguyen
(74) *Attorney, Agent, or Firm* — The Roy Gross Law Firm, LLC; Roy Gross

(57) ABSTRACT

The present disclosure relates to a device for assisting in communicably coupling a first organ body with a second organ body by employing a plurality of arc-shaped tissue connector devices comprising a tissue connector body with a proximal and distal end, and a method for manufacturing such a device. The device comprises a curved frame having a principle axis and configured to embrace, at least partially, the first organ body, the curved frame configured to receive a plurality of tissue connector devices which extend from a proximal end thereof coupled to the curved frame and terminate in a free distal end. The disclosure further relates to a tissue connector device, a holder for tissue connector
(Continued)

Figure 1:
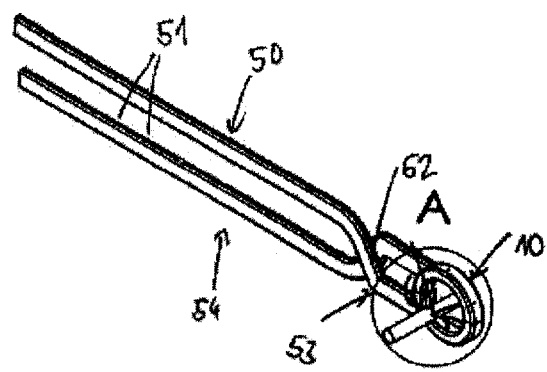

devices and a tissue-collar manipulating device, and a method of coupling a first and a second organ body using such device.

13 Claims, 15 Drawing Sheets

(30) Foreign Application Priority Data

Feb. 13, 2015 (DE) .................... 10 2015 001 819.1
Mar. 16, 2015 (DE) .................... 10 2015 003 360.3
Jul. 16, 2015 (DE) .................... 10 2015 009 224.3

(51) Int. Cl.
*A61B 17/04* (2006.01)
*A61F 9/007* (2006.01)

(52) U.S. Cl.
CPC ....... *A61B 17/11* (2013.01); *A61B 2017/0608* (2013.01); *A61B 2017/0609* (2013.01); *A61B 2017/06104* (2013.01); *A61B 2017/1107* (2013.01); *A61B 2017/1125* (2013.01); *A61B 2017/1132* (2013.01); *A61F 9/007* (2013.01)

(58) Field of Classification Search
CPC ........ A61B 17/06114; A61B 17/06061; A61B 17/06066; A61B 17/0469; A61B 17/0482; A61B 2017/1107; A61B 2017/1125; A61B 2017/1132; A61B 2017/06057; A61B 2017/06071; A61B 2017/06152; A61B 2017/06157; A61B 2017/06142; A61B 2017/06147; A61B 2017/1135; A61B 2017/1139; A61B 2017/1128; A61B 2017/1146; A61B 2017/06052; A61B 2017/06; A61B 2017/0608; A61B 2017/0472; A61B 17/06
See application file for complete search history.

(56) References Cited

U.S. PATENT DOCUMENTS

| 4,744,362 | A | | 5/1988 | Gruendler | |
|---|---|---|---|---|---|
| 5,059,207 | A | * | 10/1991 | Shah | ................ A61B 17/06066 223/102 |
| 5,554,162 | A | | 9/1996 | DeLange | |
| 5,897,572 | A | * | 4/1999 | Schulsinger | ..... A61B 17/06066 606/222 |
| 5,935,138 | A | * | 8/1999 | McJames, II | .... A61B 17/06066 606/139 |
| 2004/0050393 | A1 | | 3/2004 | Golden et al. | |
| 2005/0154401 | A1 | * | 7/2005 | Weldon | .............. A61B 17/0469 606/139 |
| 2006/0167485 | A1 | | 7/2006 | Blatter | |
| 2006/0224184 | A1 | * | 10/2006 | Stefanchik | ......... A61B 17/0482 606/222 |
| 2011/0306994 | A1 | * | 12/2011 | Bassan | ............... A61B 17/0469 606/153 |
| 2012/0010655 | A1 | * | 1/2012 | Lin | .................. A61B 17/06066 606/223 |

OTHER PUBLICATIONS

Written Opinion of ISR of PCT/IL2016/050078 completed Sep. 20, 2016; dated Dec. 16, 2016 7 pages.

* cited by examiner

DEVICE FOR COMMUNICABLY COUPLING A FIRST AND A SECOND ORGAN BODY

RELATED APPLICATIONS

This application is a National Phase of PCT Patent Application No. PCT/IL2016/050078 having International filing date of Jan. 25, 2016, which claims the benefit of German Patent Application No. 10 2015 001 656.3 filed on Feb. 10, 2015, German Patent Application No. 10 2015 001 781.0 filed on Feb. 13, 2015, German Patent Application No. 10 2015 001 819.1 filed on Feb. 13, 2015, German Patent Application No. 10 2015 003 360.3 filed on Mar. 16, 2015 and German Patent Application No. 10 2015 009 224.3 filed on Jul. 16, 2015 titled DEVICE FOR COMMUNICABLY COUPLING A FIRST AND A SECOND ORGAN BODY. The contents of the above applications are all incorporated by reference as if fully set forth herein in their entirety.

TECHNICAL FIELD

The present disclosure relates to a device for assisting in communicably coupling a first organ body with a second organ body by employing a plurality of arc-shaped tissue connector devices comprising a tissue connector body with a proximal and distal end, and a method for manufacturing such a device. The disclosure further relates to a tissue connector device, a holder for tissue connector devices and a tissue-collar manipulating device, and a method of coupling a first and a second organ body using such device.

DESCRIPTION OF RELATED ART

Surgical needles for applying sutures are well known in the art. Known needles comprise an arc-shaped needle connected to a suture thread and having a needle tip at a proximal end of the shaft. While these surgical needles are well suited for closing wounds or fixing adjacent tissues with each other, it is sometimes difficult to connect very small pieces of tissue such as segments of very small vessels or nerves, or tissues of eyes. For example, in adjoining very small diameter vessels with each other there is an inherent risk that by use of a known surgical needle opposite walls of one vessel are sutured with each other which will result in a blocking of the vessel and/or clotting of the blood.

Against this background, it is desirable to simplify the provision of stitches for connecting very small pieces of tissue.

SUMMARY

In a first embodiment, there is provided a device for assisting in communicably coupling a first organ body with a second organ body by employing a plurality of arc-shaped tissue connector devices comprising a tissue connector body with a proximal and distal end. The device comprises a curved frame having a principle axis and configured to embrace, at least partially, the first organ body, the curved frame configured to receive a plurality of tissue connector devices which extend from a proximal end thereof coupled to the curved frame and terminate in a free distal end. The first and second organ bodies may, for example, be of longitudinal extension and having a first proximal and first distal end.

In a second embodiment, the frame may be configured to receive the plurality of tissue connector devices in a cantilevered manner.

In a third embodiment, the curved frame may be configured to receive the arc-shaped needles in a way such that the tip of the needles points obliquely or radially towards the principal axis.

In a fourth embodiment, the curved frame may comprise a plurality of coupler elements configured to allow for the removable coupling of the tissue connector devices.

In a fifth embodiment, the device may further comprise a plurality of arc-shaped tissue connector devices detachably mounted thereon.

In a sixth embodiment, the arc-shaped tissue connector devices may be slidably mounted on the device in a manner such as to be slidably detachable upon sliding the needles in direction of their proximal end.

In a seventh embodiment, the arc-shaped tissue connector devices may be arranged in a cantilevered manner around the principle axis of the curved frame.

In an eighth embodiment, the arc-shaped tissue connector devices may be substantially equidistantly arranged on the curved frame.

In a ninth embodiment, the curved frame may comprise an annular-shaped body.

In a tenth embodiment, the curved frame may comprise a canted inclination with respect to the principle axis.

In an eleventh embodiment, the curved frame may comprise a plurality of complementary shaped curved frame members.

In a twelfth embodiment, the curved frame members may be detachably coupled with each other.

In a thirteenth embodiment, the plurality of curved frame members may be substantially semicircularly shaped.

In a fourteenth embodiment, the frame members may comprise a wired structure body.

In a fifteenth embodiment, the wired structure body may comprise a closed wired loop which delineates an arc-shaped contour.

In a sixteenth embodiment, the curved frame may have a concavely shaped base surface with respect to a principal axial of the curved frame.

In a seventeenth embodiment, the concavely shaped base surface has a curvature which substantially matches a convex curvature of a cornea.

In an eighteenth embodiment, the curved frame may be configured to allow for the stowing at least a portion of a suture thread.

In a nineteenth embodiment, the curved frame may be preloaded with the suture thread.

In a twentieth embodiment, the suture thread may comprise a pre-prepared knot.

In a twenty-first embodiment, the tissue connector devices may be spot-welded to the curved frame so that they can be broken off from the curved frame.

In a twenty-second embodiment, the tissue connector devices may be made from a first material different from a second material of the curved frame to which the connector devices are coupled so that connector devices broken off from the curved frame are substantially free from the second material.

In a twenty-third embodiment, the device may further comprise a user-handle.

In a twenty-fourth embodiment, the curved frame may further comprise a handle coupler element for allowing the removable coupling of a user-handle.

In a twenty-fifth embodiment, the user-handle may comprise a first and second leg coupled with each other by a scissor mechanism for removably receiving a first and second curved frame member, respectively.

In a twenty-sixth embodiment, a first and a second curved frame may be arranged in a row with respect to the principle axis.

In a twenty-seventh embodiment, the suture thread may be coiled up in such way as to hold the first and second frame together.

In a twenty-eighth embodiment, the first and second frame may comprise indentations in alignment and extending in the direction of the principle axis, the suture thread being coiled up around the frames in the indentations.

In a twenty-ninth embodiment, the first and second curved frames may be coupled together by the distal ends of the plurality of tissue connector devices.

In a thirtieth embodiment, there is provided a tissue connector device comprising an arc-shaped body having a hook-shaped end which is curved inwardly with respect to the radius of curvature of the arc-shaped body.

In a thirty-first embodiment, the hook-shaped end may be tapered.

In a thirty-second embodiment, the tissue connector device may comprise at least a portion of a suture thread.

In a thirty-third embodiment, the tissue connector device may further comprise a first arc-shaped body portion having a first hook-shaped end; and a second arc-shaped body portion having a second hook-shaped end.

In a thirty-fourth embodiment, there is provided a holder for tissue connector devices configured such that a plurality of tissue connector devices can be arranged on the holder.

In a thirty-fifth embodiment, the holder may have a curved portion.

In a thirty-sixth embodiment, the holder may further comprise another curved portion such that the holder is bifurcated.

In a thirty-seventh embodiment, the holder may comprise at least a portion of the suture thread.

In a thirty-eighth embodiment, there is provided a tissue-collar manipulating device that comprises a longitudinal body with an end for allowing the outward pulling to facilitate creating a flange-type connection between a first and second first organ body.

In a thirty-ninth embodiment, there is provided a method for manufacturing a device for coupling a first organ body of longitudinal extension and having a first proximal and first distal end with a second organ body of longitudinal extension and having a second proximal and second distal end, the method comprising: coupling a plurality of tissue connector devices to a curved frame, the tissue connector devices having an arc-shaped body having a hook-shaped end which is curved inwardly with respect to the radius of curvature of the arc-shaped body, and the curved frame having a principle axis and being configured to embrace, at least partially, the first organ body, wherein the tissue connector devices are coupled to the frame in a manner such as to extend from a proximal end thereof coupled to the curved frame and terminate in a free distal end.

In a fortieth embodiment, there is provided a method for communicably coupling a first and a second organ body using a device according to any of embodiments one to twenty-nine and/or a tissue connector device according to any one of embodiments thirty to thirty-three and/or a holder according to any of embodiments thirty-four to thirty-seven, and/or a tissue-collar manipulating device according to embodiment thirty-eight, and, optionally, wherein the method comprises: embracing, at least partially, the first organ body with the curved frame; and puncturing the first and second organ body and detaching the tissue connector devices from the frame to form the connection between the organ bodies.

In a forty-first embodiment, there is provided the use of a device according to any of embodiments one to twenty-nine and/or a tissue connector device according to any one of embodiments thirty to thirty-three and/or a holder according to any of embodiments thirty-four to thirty-seven, and/or a tissue-collar manipulating device according to embodiment thirty-eight, for communicably coupling a first organ body with a second organ body.

In a forty-second embodiment, there is provided a set for suturing human or animal tissue may comprise a device according to any of embodiments one to twenty-nine and/or a tissue connector device according to any one of embodiments thirty to thirty-three and/or a holder according to any of embodiments thirty-four to thirty-seven, and/or a tissue-collar manipulating device according to embodiment thirty-eight, for assisting in communicably coupling a first organ body with a second organ body as described.

In a forty-second embodiment, the set may be used for communicably coupling a first organ body with a second organ body.

The above embodiments are not mutually exclusive and the different optional embodiments can be combined to result in an embodiment combining different optional aspects of the device according to embodiment one and/or the tissue connector device according to embodiment thirty and/or the holder according to embodiment thirty-four and/or the tissue-collar manipulating device according to embodiment thirty-eight.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

DETAILED DESCRIPTION

The frame may be configured to receive the plurality of tissue connector devices in a cantilevered manner. The frame may additionally or alternatively be configured to receive the arc-shaped needles in a way such that the tip of the needles points obliquely or radially towards the principal axis.

The curved frame may comprise a plurality of coupler elements configured to allow for the removable coupling of the tissue connector devices.

The arc-shaped tissue connector devices may actually be mounted on the frame in a detachable manner. For example, a plurality of arc-shaped tissue connector devices may be slidably mounted on the frame in a manner such as to be slidably detachable when sliding the needles in direction of their proximal end. The tissue connector devices or needles may be engaged to the frame at the proximal end of their shaft or at another position between the proximal and the distal end. The connecting point of or bore for connecting the suture may be located between the tip of the needle and the point of engagement to the frame, or may be located beyond the point of engagement to the frame. In the case of a slidable engagement, the needle may be moved in the direction of the tip in a first step and removed from the frame in a second step. The frame may comprise guide for the sliding of the needles which is configured such that during the first step only movement in the direction of the tip is allowed and no tilting or rotation of the needle is permitted.

In case the needles are engaged to the frame are described in the foregoing paragraph, this restriction may serve to facilitate a star shaped arrangement of the stitches.

The arc-shaped tissue connector devices may be arranged in a cantilevered manner around the principle axis of the curved frame. They may be substantially equidistantly arranged on the curved frame. The tissue connector devices may be engaged to the frame such that the plane defined by the curvature of each tissue connector device stands in a radial direction. All tissue connector device pairs may be identical.

The curved frame may comprise an annular-shaped body. As such, it may adopt the shape of an optionally closed loop surrounding an opening. The loop does not have to be closed but it is sufficient for the frame to at least partially encompass the opening. The loop may be perfectly circular, but may also be elliptical or more complexly shaped. The longest diameter of the opening may be in the range of between 0.1 and 3 cm, for example, in the range of between 0.3 and 1 cm. The frame may be substantially planar in shape. It may also have a canted inclination with respect to the principle axis. It may be configured such that the distal end of the tissue connector devices extends into an opening or an area in axial alignment therewith and the needle tips are located in the opening or an area in axial alignment therewith.

The frame may comprise a plurality of complementary shaped curved frame members. These frame members may be detachably coupled with each other. The frame members may be substantially semicircularly shaped. They may be of solid makeshift or comprise a wired structure body. In case they comprise a wired structure body, the body may comprise a closed wired loop which delineates an arc-shaped contour. The frame may have a concavely shaped base surface with respect to a principal axial of the curved frame. The concavely shaped base surface may have a curvature which substantially matches a convex curvature of a cornea. The curved frame may be configured to allow for the stowing at least a portion of a suture thread. In the case of a solid body, the frame may comprise curved holes penetrating the body, which serve to slidably engage the arc-shaped tissue connector devices and at the same time serve as a guide. Accordingly, the holes may be arranged such that their curvature is as described for the curvature of the shaft of the arc-shaped tissue connector devices. Frictional engagement may aid to keep the needle in place. The frame may be made from metal such as stainless steel or polymer material for example.

As such, the frame may be divided in two or more frame members, which may be movable relative to each other to allow an opening and closing of the loop. During application of the device, this ability to open and close the loop facilitates placing the frame around the strand-shaped tissue and removing it after stitching.

The device may already be preloaded with the suture thread. The suture thread may in this case comprise a pre-prepared knot. For example, in the case of a solid frame comprising holes, the holes may also comprise a recess, for example a portion of greater diameter, which may accommodate the suture connected to the needle. The recess can be formed, for example, at the proximal end of the hole.

The tissue connector devices may be spot-welded to the curved frame so that they can be broken off from the curved frame. They may be made from a first material different from a second material of the curved frame to which the connector devices are coupled so that connector devices broken off from the curved frame are substantially free from the second material.

The device may further comprise a user-handle. The curved frame may comprise a handle coupler element for allowing the removable coupling of a user-handle. When present, the user-handle may comprise a first and second leg coupled with each other by a scissor mechanism for removably receiving the first and second curved frame member, respectively. The user-handle may serve for manual operation or as a connecting point for machine operation of the device. The support may comprise a pair of levers joined at a fulcrum. In the case of more than one frame members, the close end of each lever may be connected to one of the frame members and the far ends of the levers may serve as a handle or connecting point. The frame may be detachably connected to the support, to allow for a used frame to be replaced by a new one after a stitching procedure has been completed. The connection may be configured such that the frame can be separated from the support by movement in a direction substantially in the direction of the principal axis.

There is further provided for a device comprising two tissue connector devices connected by a common suture thread. The two tissue connector devices may be identical. They may extend in opposite directions.

In one embodiment, the device may comprise a first and a second curved frame arranged in a row with respect to the principle axis. If present, a suture thread may be coiled up in such way as to hold the first and second frame together. The first and second frame may comprise indentations in alignment and extending in the direction of the principle axis, the suture thread being coiled up around the frames in the indentations. The first and second curved frame may be coupled together by the distal ends of the plurality of tissue connector devices.

The device may comprise two or more pairs of tissue connector devices. The two tissue connector devices of each pair may extend in essentially opposite directions and be connected by a common suture thread. The two or more pairs of tissue connector devices may be arranged radially around the principal axis. The device may comprise a plurality of pairs of tissue connector devices. All tissue connector device pairs may be identical. All tissue connector devices may extend in a direction in essential alignment with the principal axis. The orientation of the arc-shaped shaft may be such that the principal axis is on the convex side thereof such that the needle tips extend obliquely or radially away from the principal axis. The longitudinal positions of all tissue connector device pairs of the device may be identical. The two tissue connector devices of each pair may be connected by a common suture, for example, at the proximal ends of their shafts. The two tissue connector devices of each pair are coplanar, the plane being defined by the curvature of the shaft. The arrangement of the tissue connector device pairs around the principal axis may be star-shaped, meaning that the planes as defined extend radially from the principal axis. The radial distribution of the tissue connector device pairs around the principal axis may be even.

The first and second curved frames may each have a central opening. One frame may embrace the first tissue connector devices of each pair and the other frame may embrace the second tissue connector devices of each pair. For example, the first and second tissue connector devices of each pair may be embraced at a central section of the shaft thereof. The frames may be perfectly ring-shaped and, for example, form a closed loop. The frames may be configured such that the loop may be opened to remove the frame from the tissue connector devices. For example, the frames may comprise two, for example, half-circle shaped jaws which are connected by a hinge at one end and detachably connected at the other end.

The frames may comprise indentations, mounting points or holes to define and freeze an even radial distribution of the tissue connector devices inside the opening. The frames and the tissue connector devices may be slidable with respect to each other in a direction parallel to the principal axis.

A method for communicably coupling a first and a second organ body using a device as described above is also provided. The method comprises embracing, at least partially, the first organ body with the curved frame; and puncturing the first and second organ body and detaching the tissue connector devices from the frame to form the connection between the organ bodies.

A tissue-collar manipulating device may also be provided. It may comprise a longitudinal body with an end for allowing the outward pulling to facilitate creating a flange-type connection between a first and second first organ body. The tissue-collar manipulating device may comprise a support and a disc shaped head having indentations at regular intervals along its circumference. The tissue-collar manipulating device may serve to define and freeze an even radial distribution of tissue connector devices around the principal axis.

A set for suturing human or animal tissue may comprise a tissue-collar manipulating device as described and a device as described. It may serve for connecting two loose ends of a blood vessel.

A tissue connector device may in one embodiment also be provided. It may be used in conjunction with any of the above described embodiments. The tissue connector device may comprise an arc-shaped body having a hook-shaped end which is curved inwardly with respect to the radius of curvature of the arc-shaped body. The hook-shaped end may be tapered. The tissue connector device may comprise at least a portion of a suture thread. The tissue connector device may comprise a first arc-shaped body portion having a first hook-shaped end and a second arc-shaped body portion having a second hook-shaped end.

The tissue connector device may comprise a shaft having a tip portion which is to a main portion and comprises a tip. The tip may be angled in relation to the main portion at an angle of, e.g., smaller 180°. There may be no steady continuation of the shaft as regards the curvature of a main portion of the shaft, but the shaft may be bent backwards, so that the tip extends at an angle in relation to a main portion of the shaft. The longitudinal axis of the tip may be angled in relation to a main portion of the shaft. The shaft of the tissue connector device may be composed of at least two portions, namely of a main portion which may be held by a surgeon and a tip portion which comprises the tip. The tip may be angled in relation to the curvature of the main portion in an angle ranging from, e.g., 30° to 110° or ranging from, e.g., 45° to 90°. The curvature of the main portion may be substantially constant. The tip portion may be curved or straight. The transition between the main portion and the tip portion of the shaft may be continuous or sudden. The tip may have any shape which is suitable for the purpose of providing a suture. For example the tip may be cone-shaped or may have a number of cutting edges.

The main portion and the tip portion of the shaft may constitute one integral part. Alternatively, the main and the tip portions of the shaft may be manufactured as separate parts which are detachably connected to each other.

The shaft may comprise a bore for attaching a suture thread. The bore may be located at the proximal portion of the shaft. The main portion of the shaft may extend beyond the bore for attaching the suture thread and may serve as a handle or attachment portion for a handle.

The use of a tissue connector device as described above for communicably coupling a first and a second organ body is also provided.

A holder for tissue connector devices may also be provided herein. The holder may be configured such that a plurality of tissue connector device can be arranged on the holder. The holder may have a curved portion. The holder may also comprise another curved portion such that the holder is bifurcated. The holder may also comprise at least a portion of a suture thread.

DESCRIPTION OF DRAWINGS AND EXAMPLES

Figure 2:
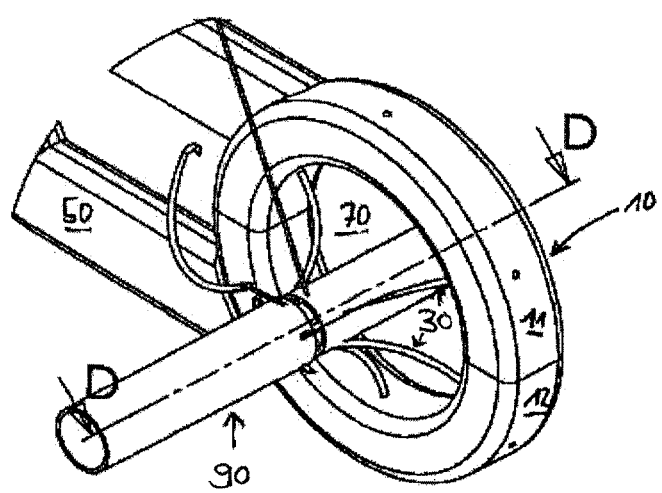
Figure 3:
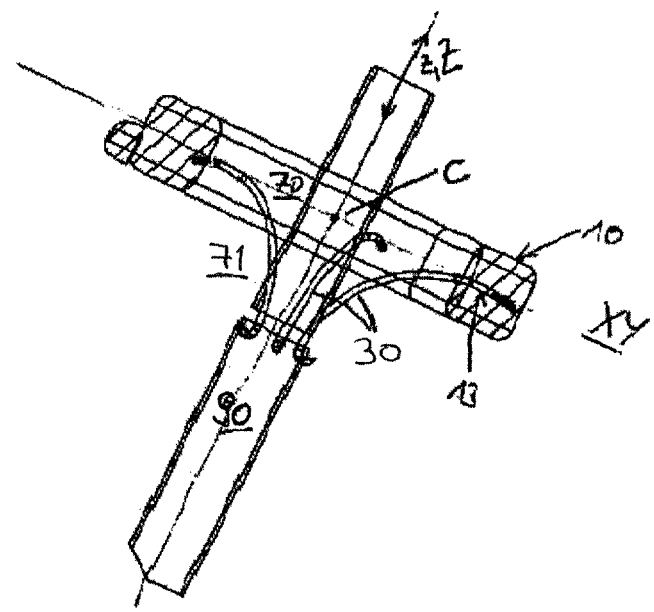
Figure 4:
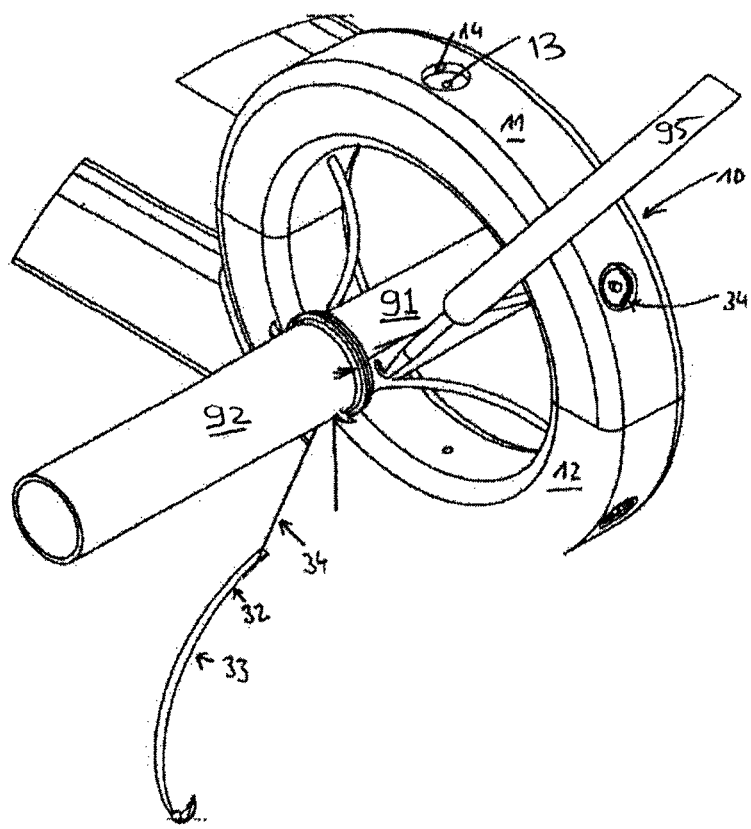
Figure 5:
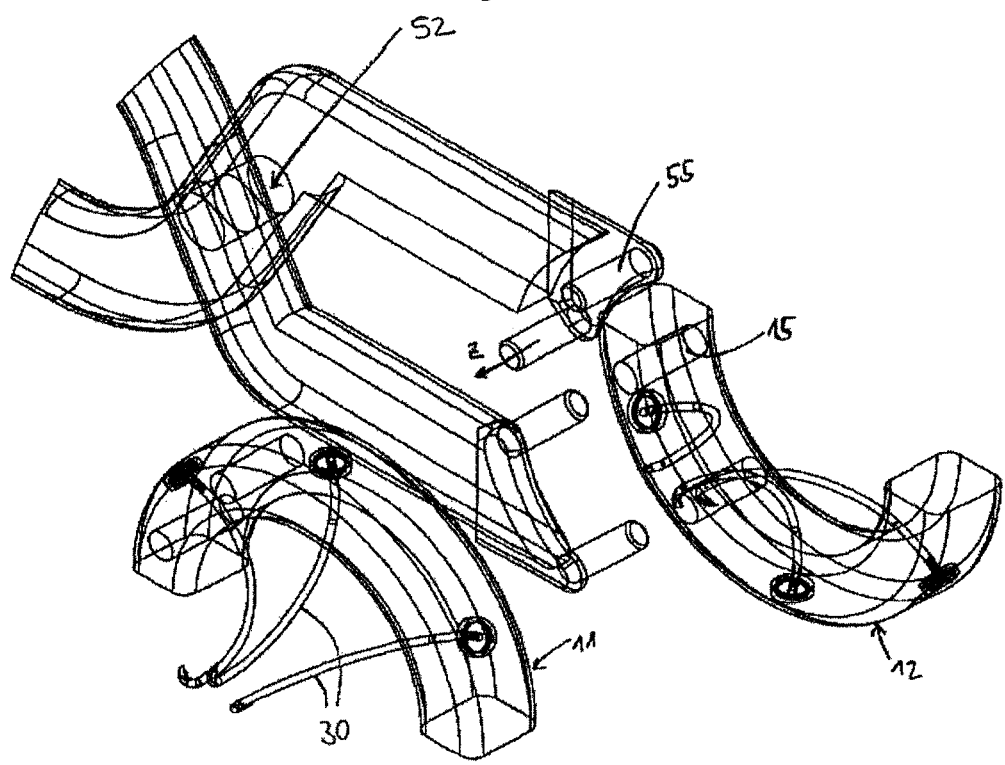
Figure 6:
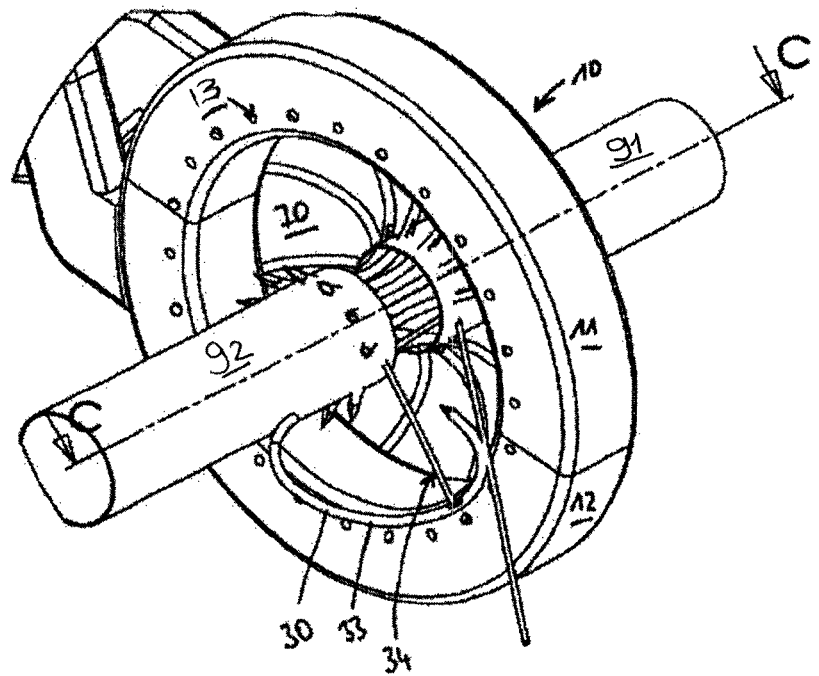
Figure 7:
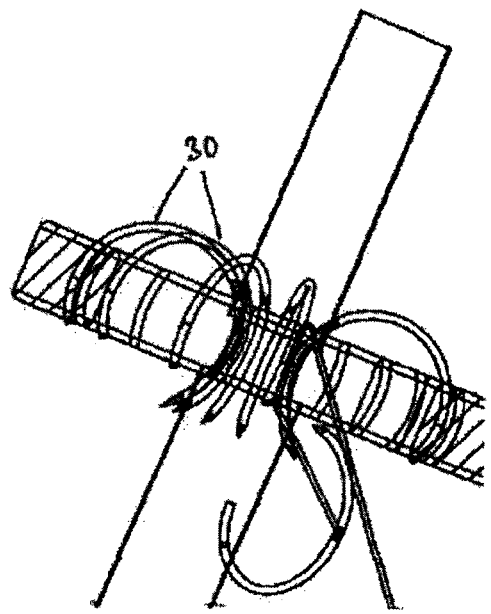
Figure 8:
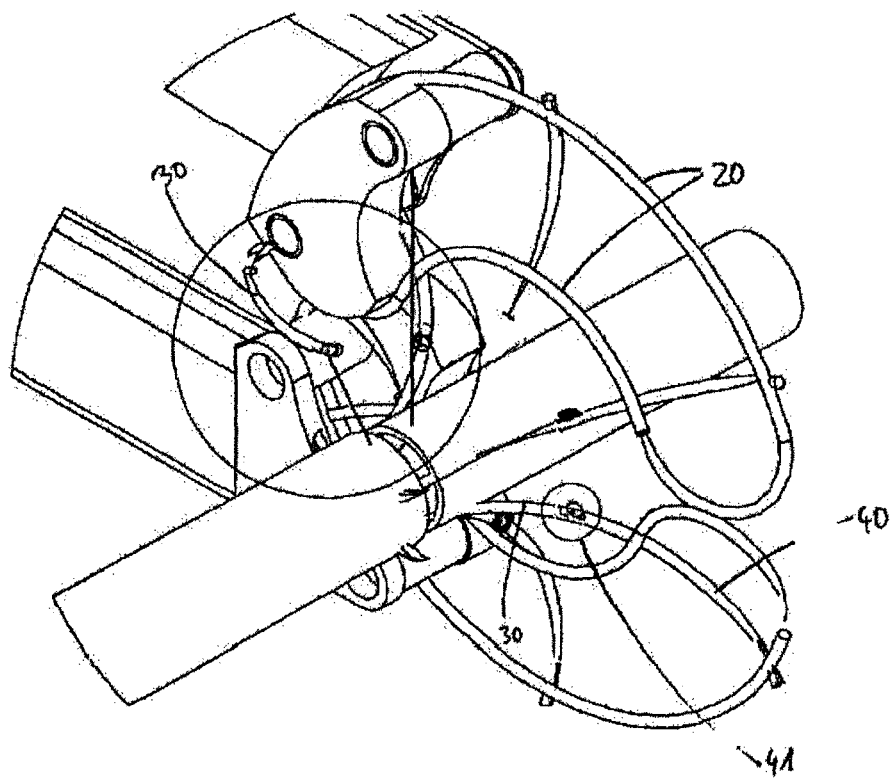
Figure 9:
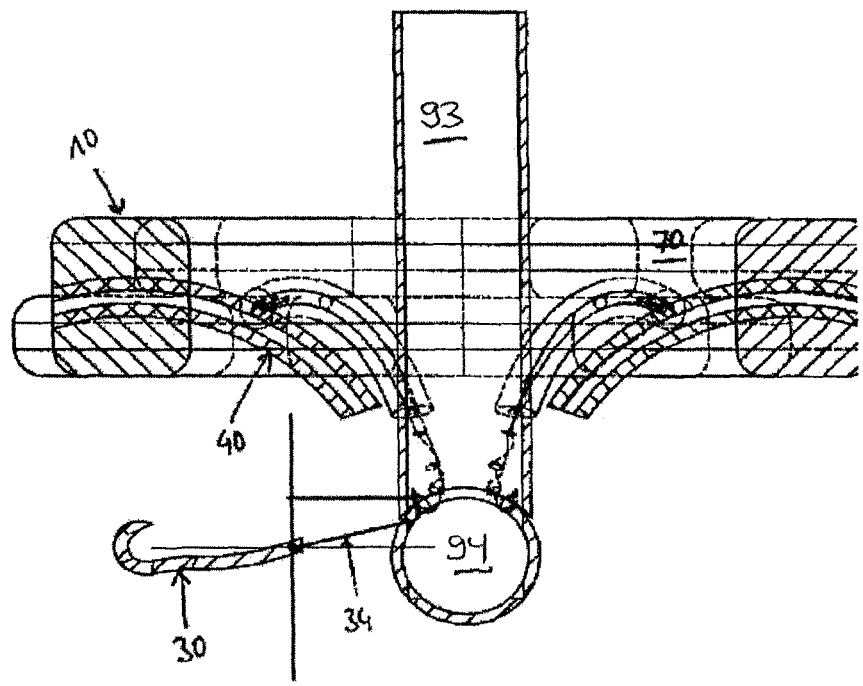
Figure 10:
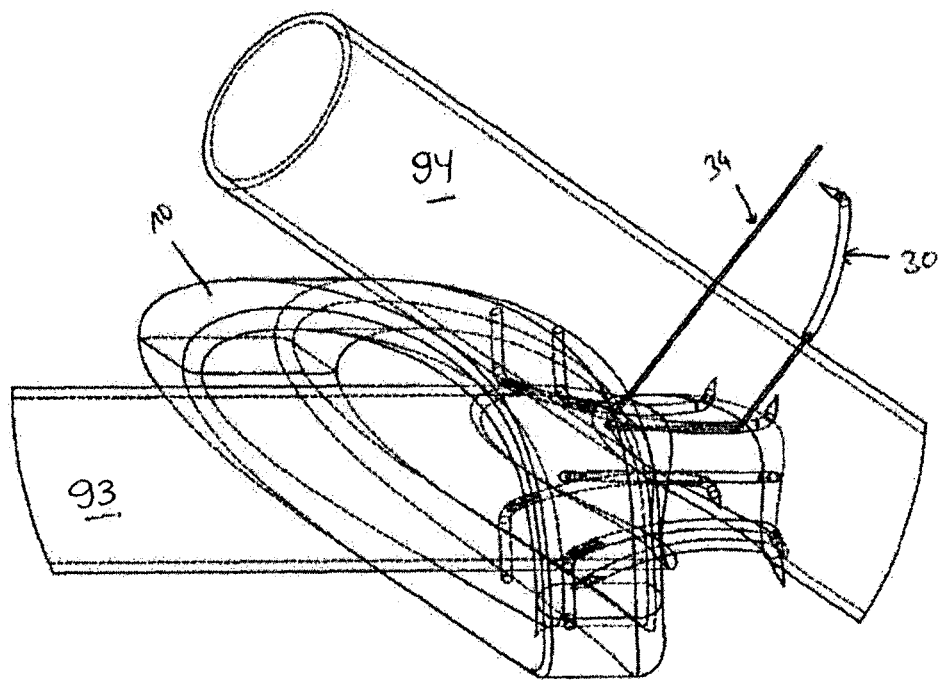
Figure 11:
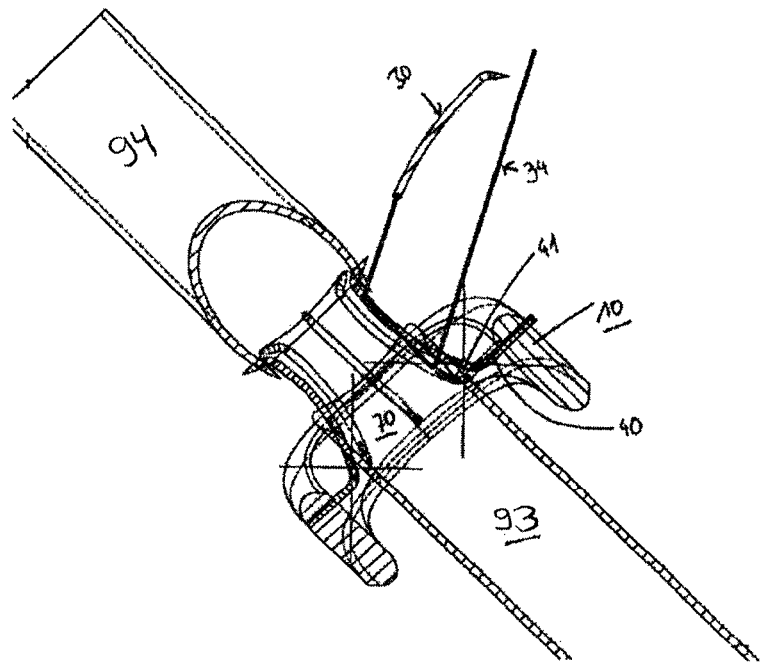
Figure 12:
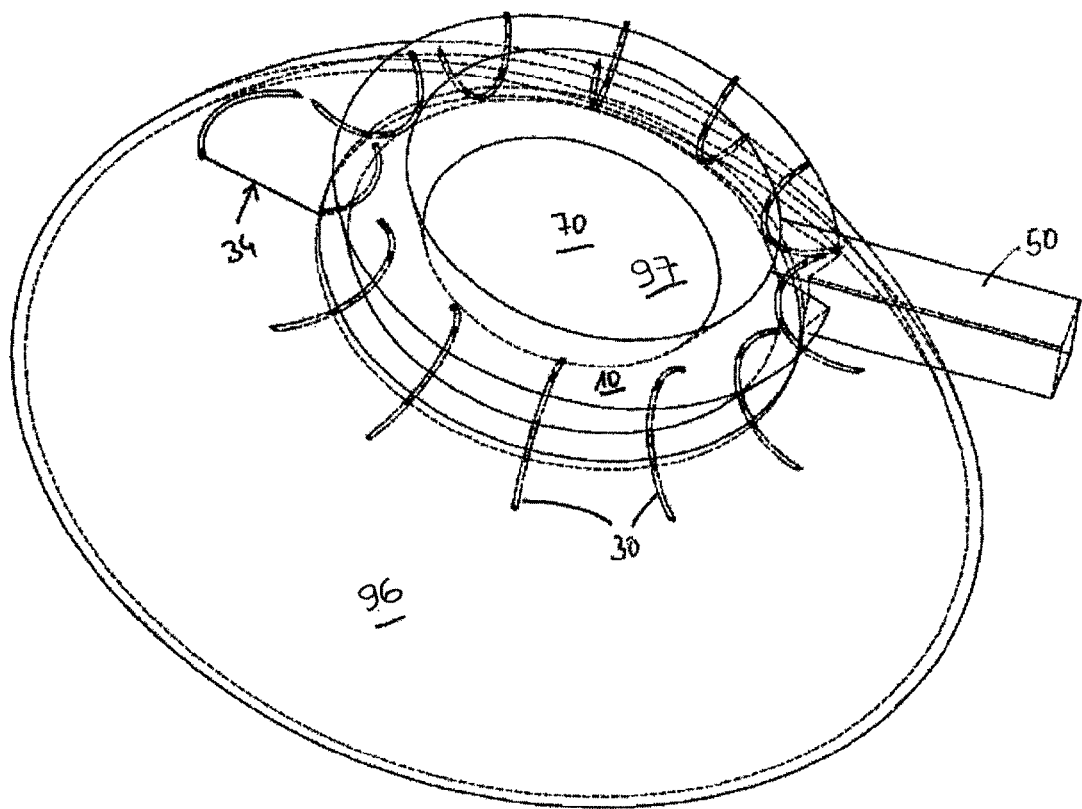
Figure 13:
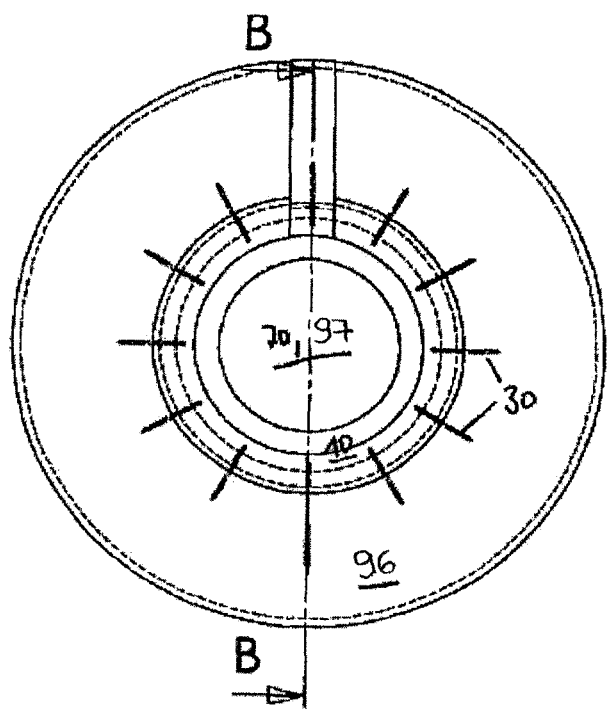
Figure 14:
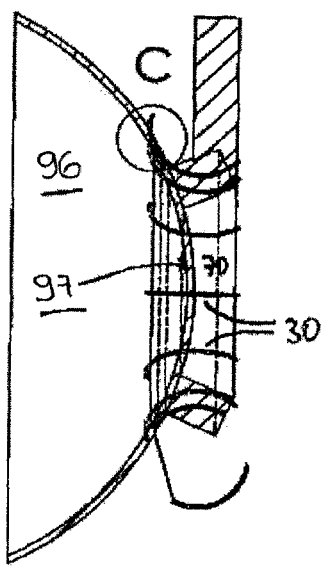
Figure 15:
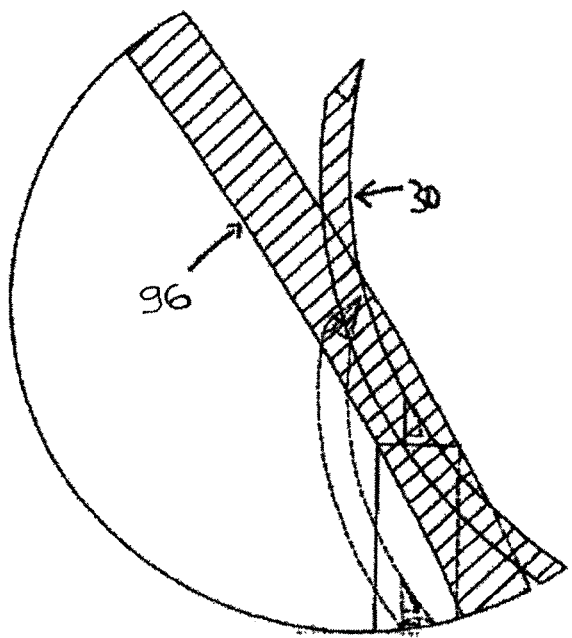
Figure 16:
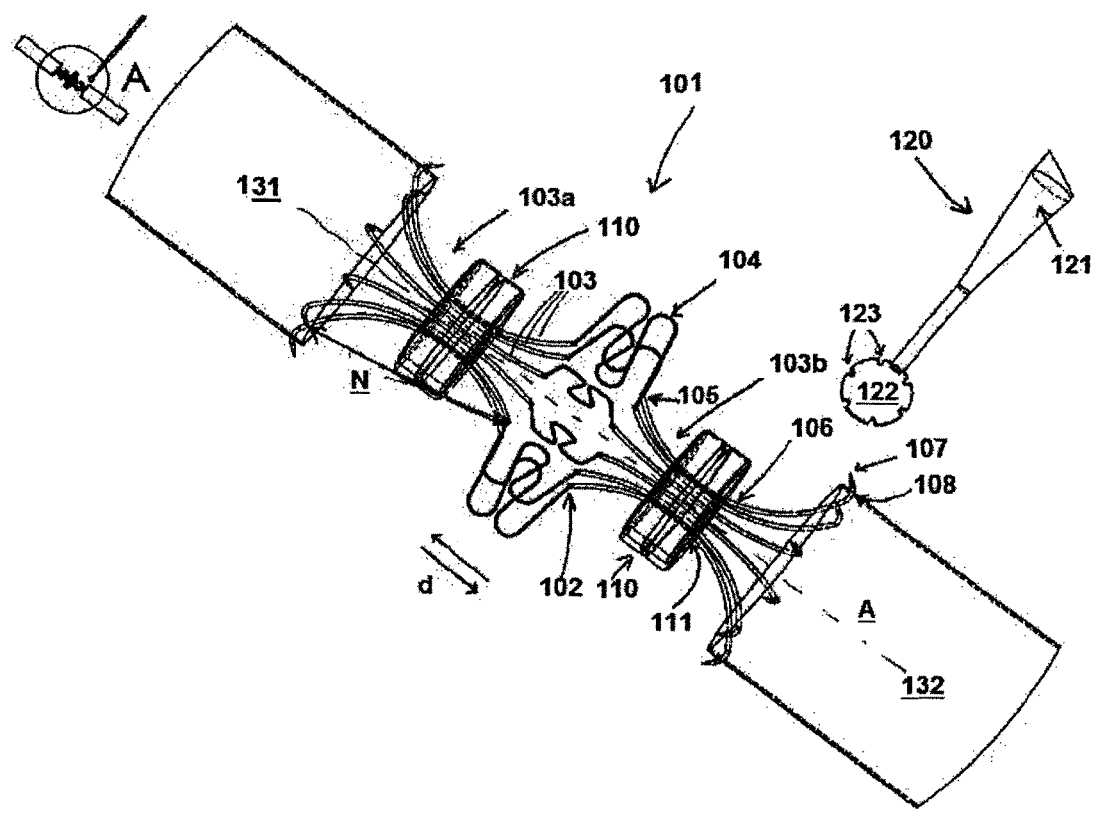
Figure 17:
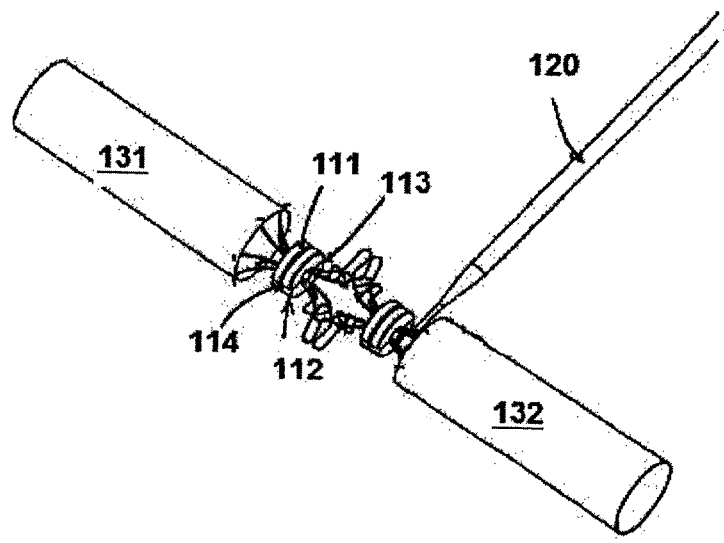
Figure 18:
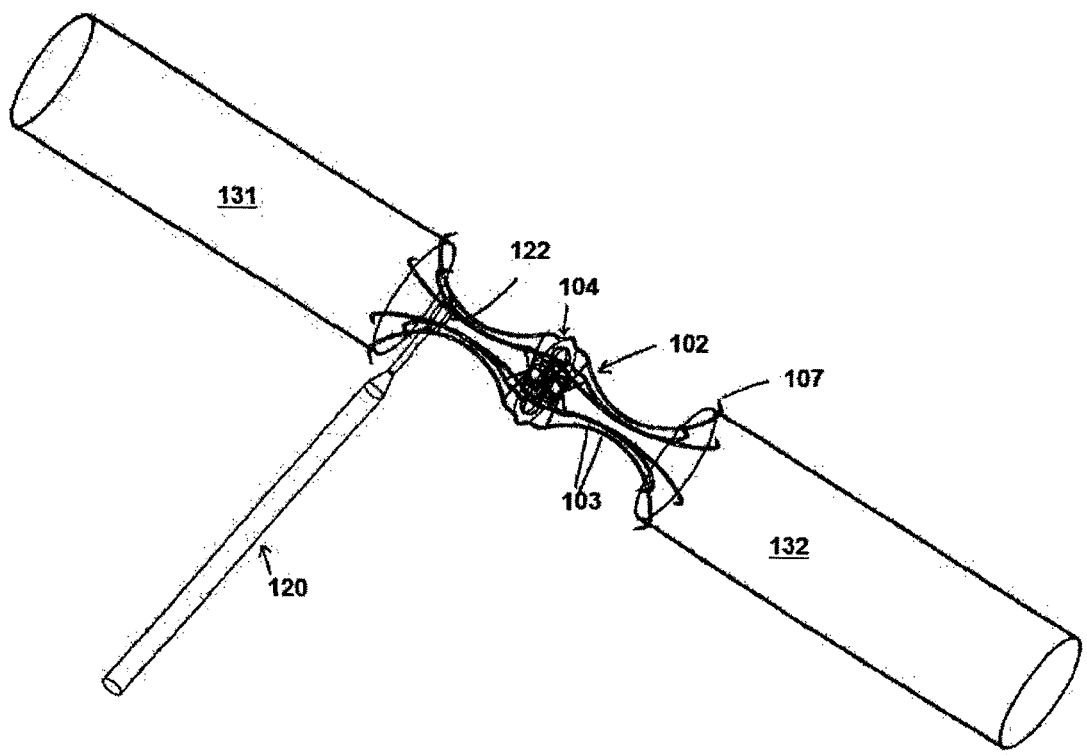
Figure 19:
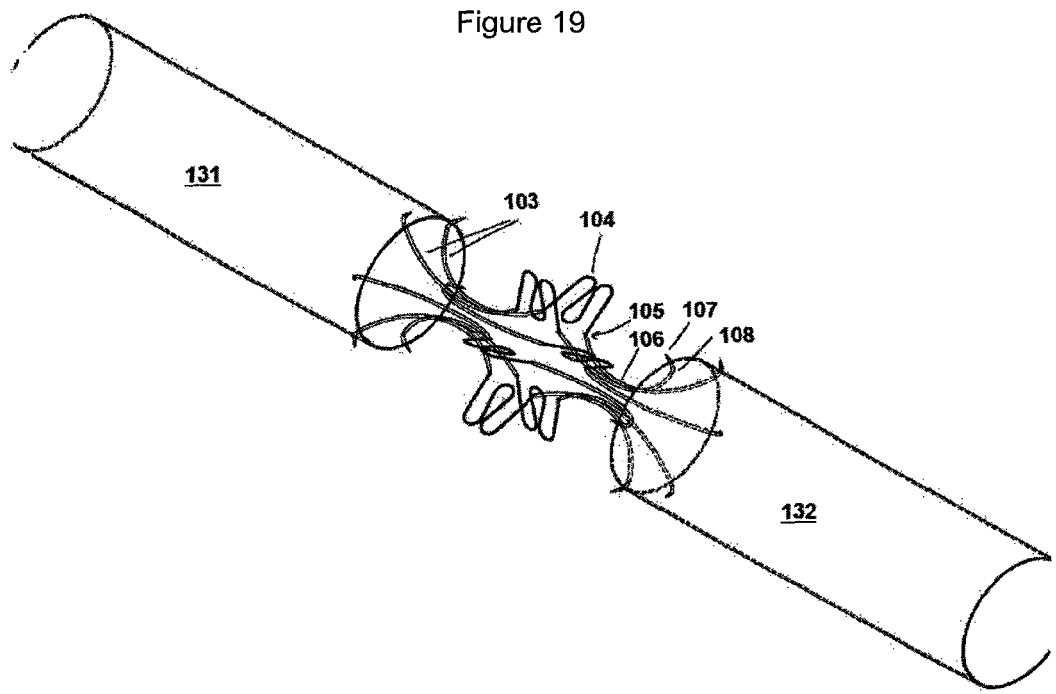
Figure 20:
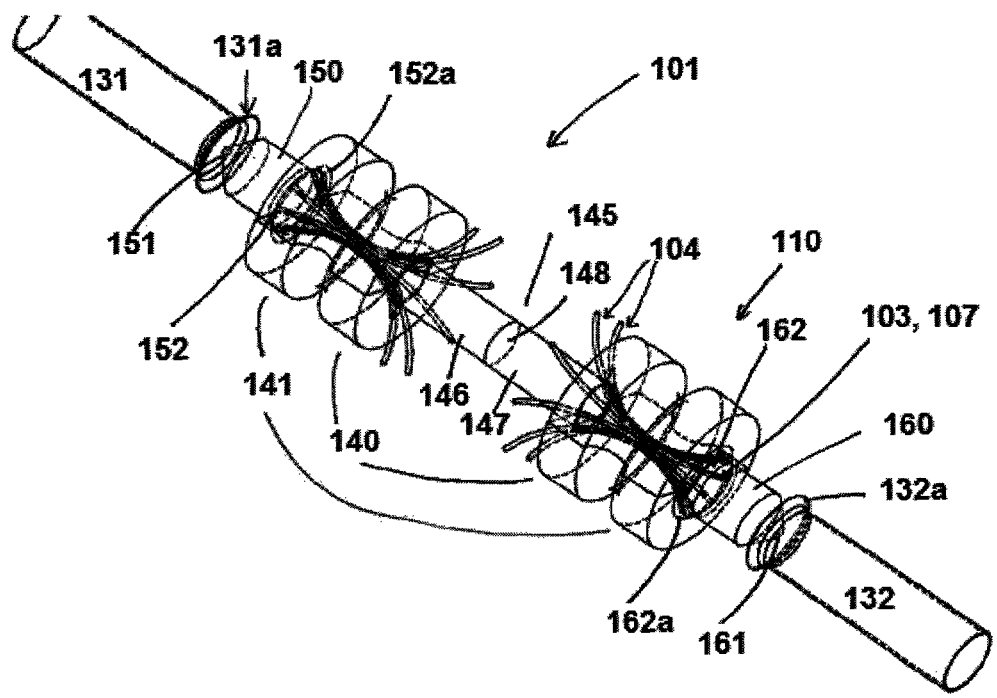
Figure 21:
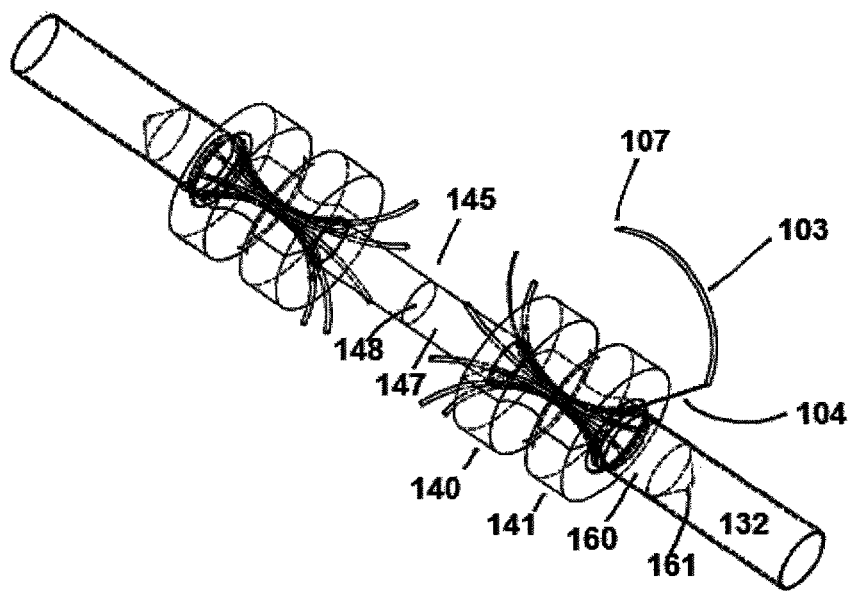
Figure 22:
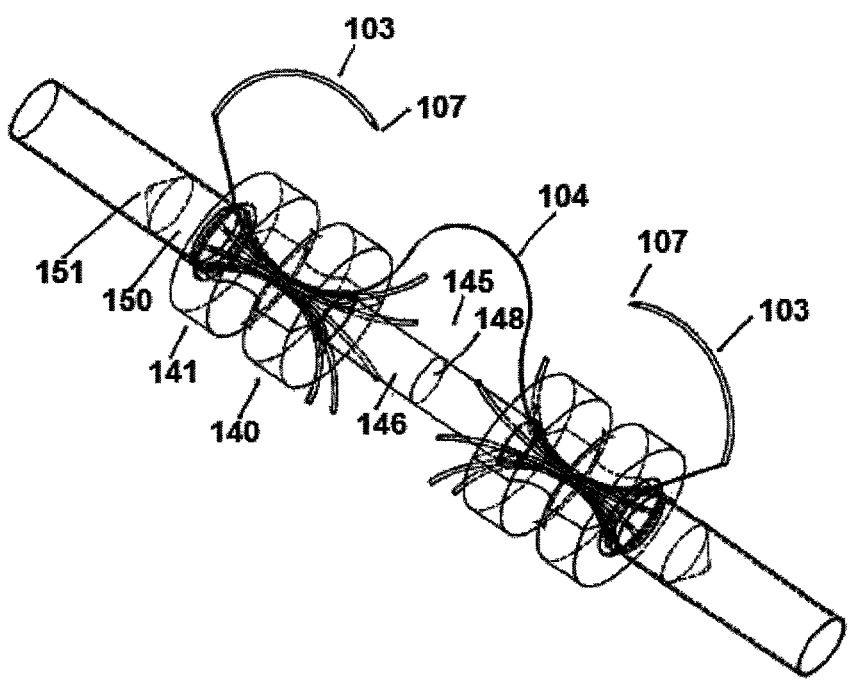
Figure 23:
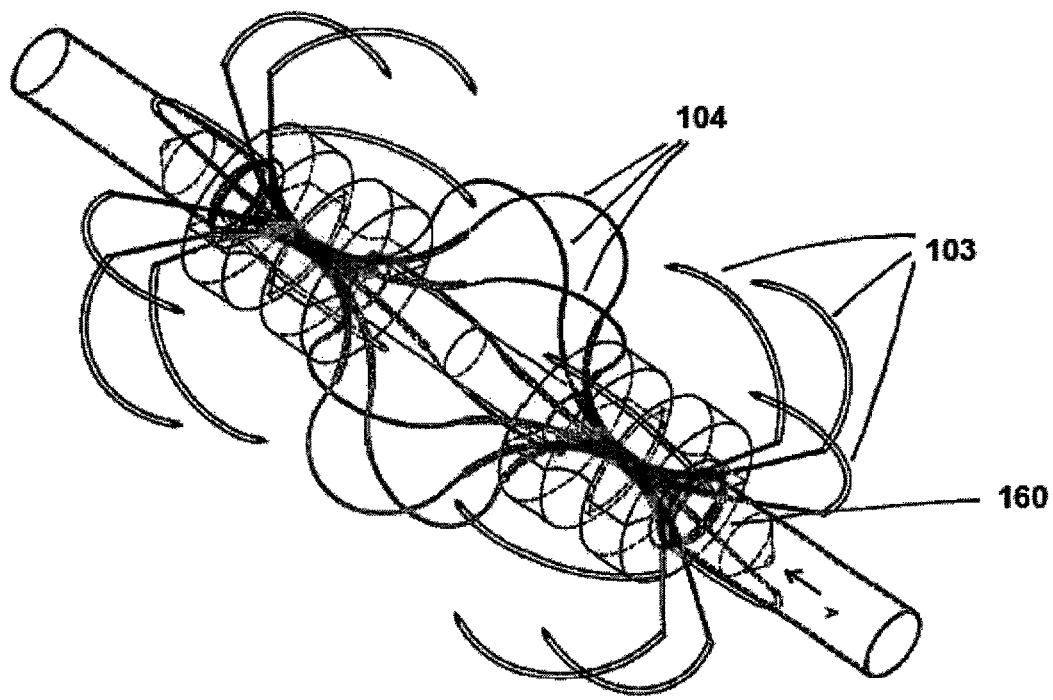
Figure 24:
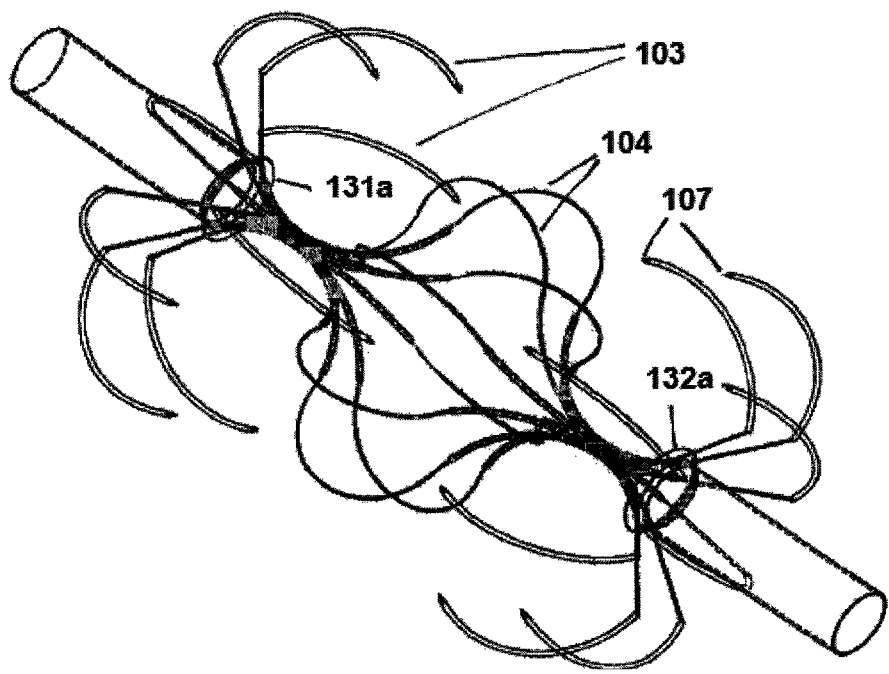
Figure 25:
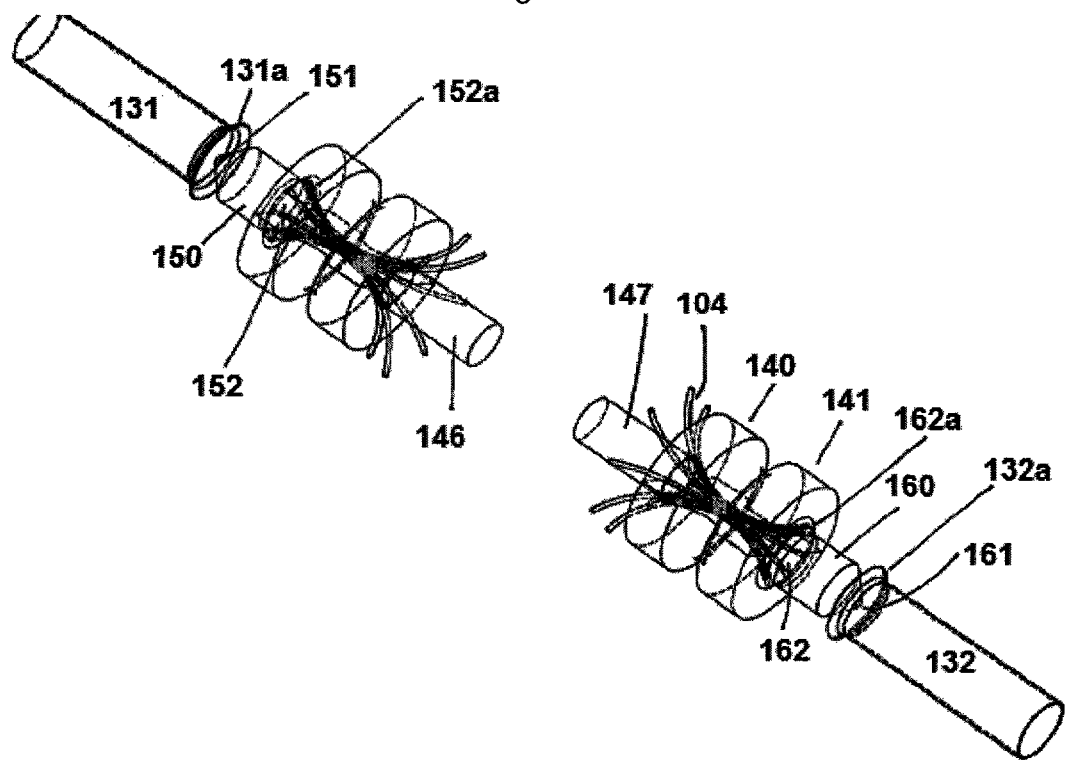
Figure 26:
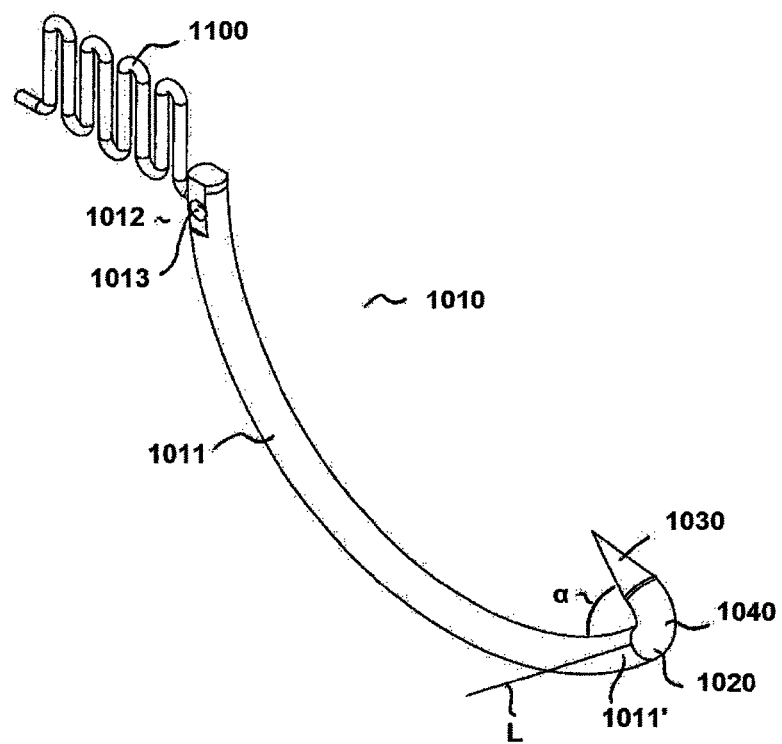
Figure 27:
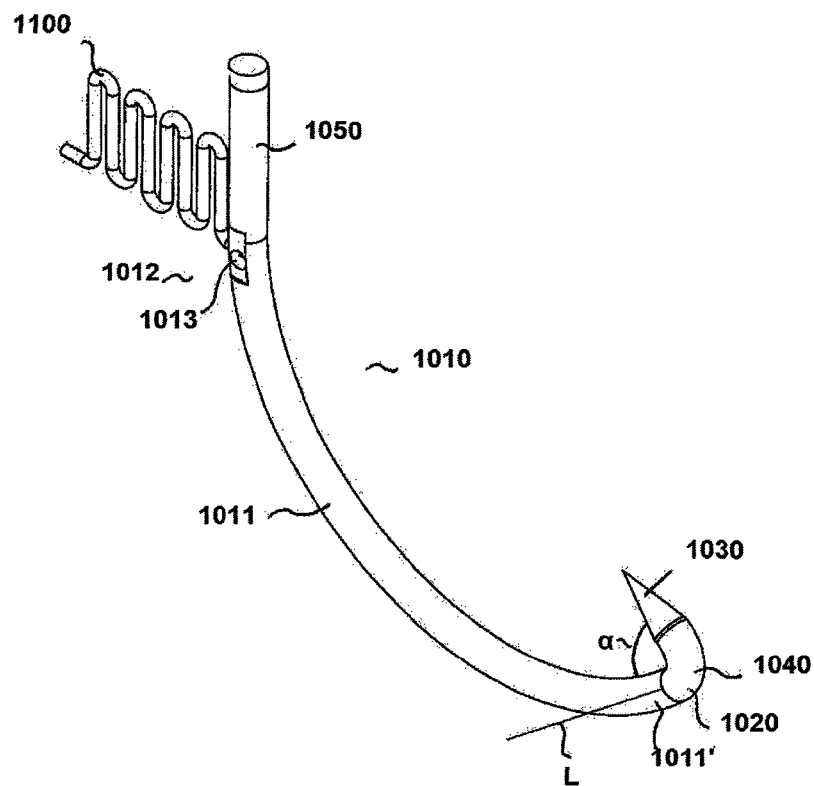
Figure 28:
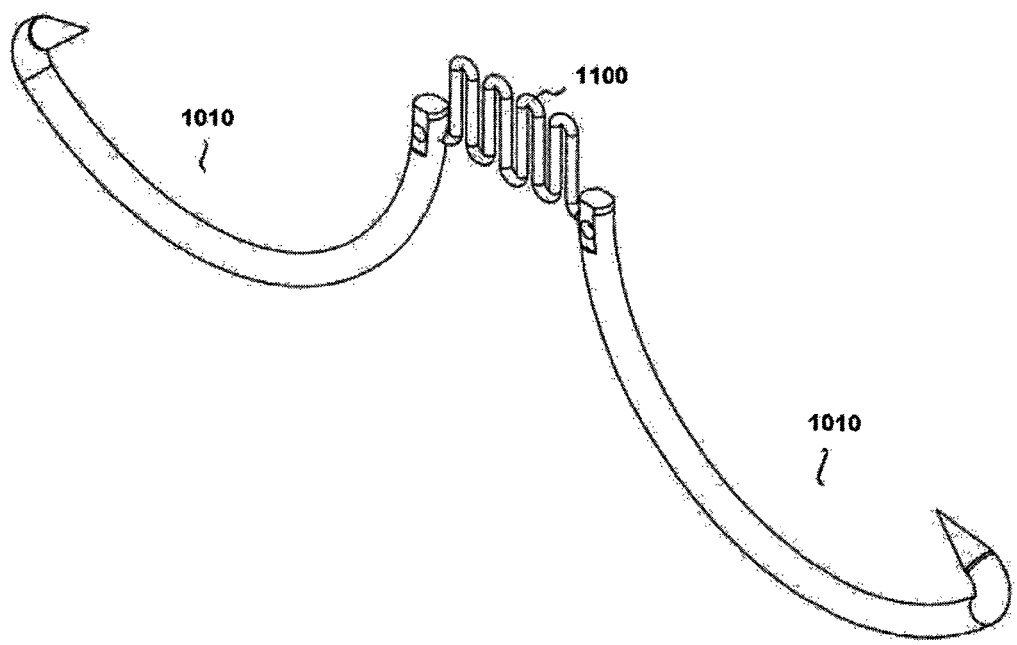
Figure 29:
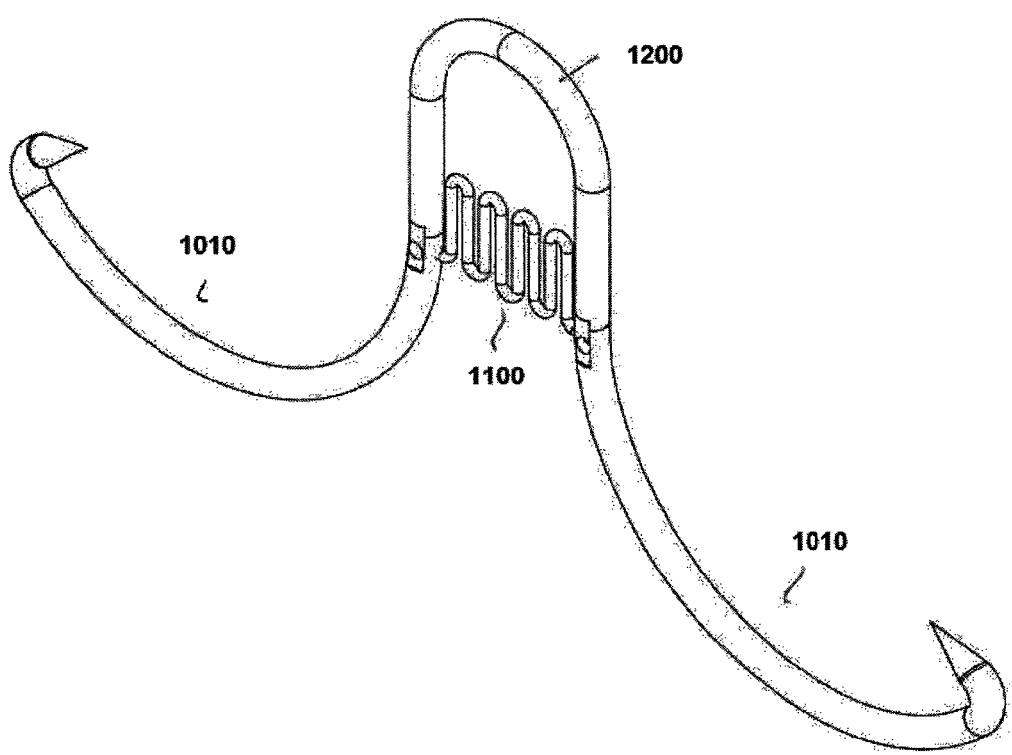

Further details are hereinafter described with reference to a number of working examples and figures. The figures show:

FIG. 1: a schematic perspective view of a first embodiment of a device for assisting in communicably coupling a first and a second organ body;

FIG. 2: an enlarged view of the window A thereof;

FIG. 3: a longitudinal cut along the line D-D of FIG. 2;

FIG. 4: a further schematic perspective view during a more advanced stage of the coupling procedure;

FIG. 5: a further schematic perspective view wherein the frame is detached from the user-handle;

FIG. 6: an enlarged schematic perspective view of the frame and the needles of a second embodiment of a device for assisting in communicably coupling a first and a second organ body;

FIG. 7: a longitudinal cut along the line C-C of FIG. 6;

FIG. 8: an enlarged schematic perspective view of the frame and the needles of a third embodiment of a device for assisting in communicably coupling a first and a second organ body;

FIG. 9: a longitudinal cut through the frame of a fourth embodiment of a device for assisting in communicably coupling a first and a second organ body;

FIG. 10: a schematic perspective view of a fifth embodiment of a device for assisting in communicably coupling a first and a second organ body;

FIG. 11: a longitudinal cut through the frame of the fifth embodiment;

FIG. 12: a schematic perspective view of a sixth embodiment of a device for assisting in communicably coupling a first and a second organ body;

FIG. 13: a schematic top view on the device of FIG. 12;

FIG. 14: a longitudinal cut through the device of FIG. 12;

FIG. 15: an enlarged schematic view to the area C of FIG. 14;

FIG. 16: a perspective schematic view of a sixth embodiment of a device for assisting in communicably coupling a first and a second organ body;

FIG. 17: the same embodiment during an advanced stage of the suturing procedure;

FIG. 18: the same embodiment during a further advanced stage of the suturing procedure;

FIG. 19: the same embodiment during an again more advanced stage of the suturing procedure;

FIG. 20: a perspective schematic view of a seventh embodiment of a device for assisting in communicably coupling a first and a second organ body;

FIG. 21: the same embodiment during an advanced stage of the suturing procedure;

FIG. 22: the same embodiment during a further advanced stage of the suturing procedure;

FIG. 23: the same embodiment during a still further advanced stage of the suturing procedure;

FIG. 24: the same embodiment during an again more advanced stage of the suturing procedure;

FIG. 25: a perspective schematic view of an eighth embodiment of a device for assisting in communicably coupling a first and a second organ body;

FIG. 26: a schematic perspective view of a tissue connector device with a suture thread connected therewith, FIG. 27: a further schematic perspective view of a tissue connector device with a suture thread connected therewith;

FIG. 28: a schematic perspective view of a system comprising two tissue connector devices according to FIG. 26 being linked by a suture thread; and FIG. 29: a schematic perspective view of a system comprising two tissue connector device according to FIG. 26 being linked by a suture thread and a connection portion.

According to embodiments, the device schematically shown in FIGS. 1 to 5 comprises a curved frame 10 operative to receive a plurality of tissue connector devices in the form of surgical needles 30. The frame is connectable to a user-handle 50 for manual operation. The frame comprises an annular-shaped body and defines an opening 70 which encompasses a blood vessel 90 to be sutured.

The frame 10 may be constituted by an annular ring. It may be constituted by two complementary shaped curved frame members 11 and 12, which are identical and adopt the shape of a half ring, together forming a closed loop. The both frame members 11 and 12 are solid bodies and comprise curved holes 13 which serve to engage the needles 30, as described hereinafter.

In some embodiments, each frame member may be individually mounted to user-handle 50 and movable relative to each other to allow an opening and closing of the ring. The user-handle 50 comprises a pair of levers 51 joined at a fulcrum 62, the proximal end 53 of each lever being connected to one of the frame members and the distal ends 54 of the levers with respect to the frame members serving as the handle. As apparent particularly from FIG. 5, the frame members 11 and 12 may be detachably connected to the user-handle 50 via a plug-in connection, comprising for example a plurality of pins 55 and corresponding recesses 15. This allows for used frame members, which are devoid of needles, to be replaced by new frame members to continue stitching using the same user-handle after one procedure has been completed. The pins and recesses extend in the direction of the principal axis z such that the frame members can be separated from the support by movement in the direction of the principal axis. Both the frame and the user-handle may be made from stainless steel for example or of any other suitable material.

In some embodiments, the needles 30 are for example evenly distributed over the circumference of the opening. They extend, when coupled to the frame(s), into the opening 70 and an area 71 in axial alignment with the opening 70, the needle tips 31 being located within the area 71. The plane Z defined by the curvature of each needle is spanned by the vector in direction of the principal axis z and a radial vector in the XY plane defined by the frame. In some embodiments, the proximal end 32 of the arc-shaped shaft 33 of a needle is detachably engaged a frame member at. One or more needles (e.g., three needles) may be detachably engaged with at least one of the frame members.

In some embodiments, the distal end of the needle's shaft is provided with the needle tip. A suture thread 34 is connected to the proximal end of the shaft. In some embodiments, the shaft may comprise a non-uniform curvature. The curvature of the distal end section may for example be significantly higher than the curvature of the central section.

The detachable engagement of the needles 30 to the frame 10 is best apparent from FIGS. 3 and 4. In some embodiments, the solid body of the frame 10 comprises curved holes 13 in which the proximal section of the curved shaft 33 of the needles 30 is slidably engaged, e.g., in a frictional manner. Additional or alternative coupling mechanism may be employed. In some embodiments, the holes 13 fully traverse the body of the frame. In some other embodiments, the holes 13 only partially traverse the body the frame. At the back end the holes 13 comprise in some embodiments a portion 14 of greater diameter to accommodate the suture thread 34 of the needle.

Upon application of the device, the surgeon holds in some embodiments on to the user-handle 50 and moves the frame 30 to one segment 91 of the desired vessel 90 to be stitched. The user-handle is operated to separate the two frame members 11 and 12 and open the ring, such that the vessel can be placed inside the opening 70. The user-handle is then operated to close the ring. Depending on the dimensions and on how close the needle tips are to the center C of the opening, the needles 30 already puncture the vessel segment 91. In case the vessel segment is not already punctured, the needles 30 are slid out of the holes 13 (e.g., pulled or pushed using suitable tools) until all needles puncture the vessel segment 91. Care should be taken that the vessel is punctured close to the loose end to be connected. As the proximal section of the needle shaft is still inside the hole 13, no tilting or rotation of the needle is permitted, which allows for an even puncturing of the vessel. The vessel segment 91 is then firmly held in place without the need for additional tools. Vessel segment 91 is then brought in alignment with vessel segment 92, which is held in place by, for example, a clamp or the like. The needles 30 are then, one by one, slid out of the holes 13 completely to complete the stitches. The curvature and mounting position of the needles is such that the orientation of the distal portion of the needle shaft becomes more axial with increasing proximity to the tip, such that the tips already point in the correct direction before this working step is initiated. In the first part of that movement, when the at least some of the proximal section of the needle shaft is still inside the hole 13, no tilting or rotation of the needle is permitted, which supports correct movement and aids not to puncture the opposite end of the vessel. It is apparent that the needles are configured and engaged to the frame such that the needle tips may approximate the center C of the opening very closely, e.g., by less than a millimeter, but not reach or cross it. During the second part of that movement, the needle is then freely moved and tilted to complete the stitch. Tissue-collar manipulating device 95 may be used as a further support. Lastly, the user-handle is again operated to separate the two frame members 11 and 12 and open the ring, such that the device can be removed from the stitched vessel 90.

The fact that all needles and the vessel are firmly held in place for each of the stitches, and the fact that the movement of the needles is, at least partially guided, allows for a more precise outcome of the procedure.

In the further embodiments according to FIGS. 6 to 11, only differences to the embodiment of FIGS. 1 to 5 will be discussed. Reference numerals are designated as in FIGS. 1 to 5.

FIGS. 6 and 7 show an embodiment, wherein the holes 13 in the frame 10 run substantially in the direction of the principal axis and wherein the needles 30 are longer and have a curvature covering more than 180° for example. The curvature is substantially uniform over the whole length of the needle shaft 33. A suture thread 34 is connected to the shaft between its engagement point with the frame and its distal end. This allows for an even more precise operation as the movement of the needles is also guided when they exit the second vessel 92. However, it may not be possible to puncture the first vessel already upon closing the frame 10, but it may be necessary to slide the needles before the first vessel 91 is fixed.

FIG. 8 shows an embodiment where the frame in this embodiment does not comprise solid bodies but is a wired structure body 20 to which the needles 30 are engaged. The needles are detachably engaged to a needle stub 40 which resembles a continuance of the needle shaft. The connection 41 between the needle stub 40 and the needle 30 is a mechanical connection. The suture thread 34 is connected to the needle at the proximal end. Once the device is applied to the vessel, and the needles have punctured the vessel upon closing of the frame, the needles 30 are disengaged from the stub and the stitches completed one by one.

The embodiments shown in FIGS. 1 to 8 are, for example, suited for connecting two loose ends of a strand-shaped piece of tissue such as a blood vessel. During such application, the device is arranged such that the segments 90 pass the opening 70 in direction Z of the principal axis and are encompassed by the frame 10. Suturing blood vessels has been selected as a representative embodiment and the same procedure as described above may be conducted using nerves and the like.

In this embodiment of FIG. 9 the needles 30 are shorter than the needles of the previous embodiments and, optionally, hook-shaped. The frame is equipped with hollow needle stubs 40 which are tubes curved in a manner as described for the needle shafts in the embodiment of FIGS. 1 to 5. The short needles are slidably engaged inside the needle stubs, with the suture thread 34 being connected to the proximal end of the needles. Due to the configuration of the needle stubs and the needles, the embodiment shown in FIG. 9 is, for example, suited for connecting for connecting a loose end of a strand-shaped piece to a hole in a continuous strand-shaped piece of tissue 94 such as a blood vessel (e.g., 3-way connection). During such application, the device is arranged such that the loose segment 93 passes the opening 70 in a direction Z of the principal axis and is encompassed by the frame 10. Suturing blood vessels has been selected as a representative embodiment and the same procedure as described above may be conducted using nerves and the like.

FIGS. 10 and 11 show a further embodiment suitable for forming three-way connections for example, optionally for obliquely connecting a loose end of a strand-shaped piece to a hole in a continuous strand-shaped piece of tissue. One significant difference over the embodiment discussed before is the non-circular and not fully planar shape of the frame 10, which serves to avoid spatial obstruction when obliquely connecting a loose end of a strand-shaped piece to a hole in a continuous strand-shaped piece of tissue. The engagement of the needles to the frame is as discussed in connection with FIG. 8.

FIGS. 12 to 15 show an embodiment suitable for connecting patch-shaped tissue, for example, the cornea to the sclera.

In one embodiment, the needles are engaged to the frame such that they axially or obliquely extend from the frame and the needle tips are located beyond the plane defined by the frame. This embodiment of the device is, for example, suited for connecting patch-shaped tissue, for example, the cornea to the sclera. The frame may adopt any shape corresponding to the shape of the tissue patches which are intended to be sutured. A loop surrounding an opening may be employed also in this embodiment as it allows to access the needles and to have an unobstructed view from two sides. In this embodiment, the frame may be formed as one integral part, as after stitching no removal of the device from a strand-shaped tissue sitting in the opening is required.

The frame 10 is formed as one single piece and the user-handle 50 is a simple rod. The frame is substantially circular with each of its walls slightly tilted in order to resemble shape of the eyeball. The needles, contrary to the foregoing embodiments, not extend into the opening, but obliquely extend from the frame such that the needle tips are located beyond the plane defined by the frame. The needles have a constant curvature and the curvature extends over, e.g., more than 120°.

Upon application of the device according to FIGS. 12 to 15, the surgeon holds on to the user-handle 50 and moves the frame 30 to axially approach and contact the eyeball 96 such that the central opening 70 is in alignment with the cornea 97 to be attached. During the approach, the needles 30 already puncture the cornea. The cornea is then firmly held in place without the need for additional tools. The needles 30 are then, one by one, slid out of the holes 13 completely to complete the stitches. In the first part of that movement, when the at least some of the proximal section of the needle shaft is still inside the hole 13, no tilting or rotation of the needle is permitted, which supports correct movement.

The device shown in FIGS. 16 to 19 is generally designated with numeral 101 and comprises a plurality of pairs 102 of identical needles 103. In some embodiments, the two needles of each pair are connected by a common suture thread 104 at the proximal ends 105 of their shafts. The needles 103 comprise a curved shaft where the distal end is provided with a needle tip. The suture thread 104 is permanently connected to the shaft at the proximal end 105 thereof. The shaft comprises a non-uniform curvature for example, wherein the angle between the orientation of the tip 107 and the orientation of a central section 106 of the shaft ranges, for example, from 45° to 90°. The curvature of the central section is substantially constant and the curvature of the distal section 108 adjacent to the tip is higher than the curvature of the central section. The needle may be integrally formed as a one-piece needle body from stainless steel for example or any other suitable material. The two or more pairs of needles are arranged radially around a common longitudinal axis A.

In some embodiments, the two needles belonging to each pair extend in opposite directions meaning that the directions N of the needles confine an angle of, e.g., 140° or more (the 'direction of a needle' being understood as the imaginary line from the proximal to the distal end of the needle). All needles extend essentially in the direction of the principal axis such that the offset between the direction N of the needles and the direction of the principal axis A is less than, e.g., 20°. The longitudinal positions d of all needle pairs of the device are identical. For example, the longitudinal positions of the first needles 103a of each pair and the longitudinal positions d of the second needles 103b of each pair are identical.

The orientation of the needles 103 is such that the longitudinal axis A is on the convex side of the needles. The two needles 103 of each pair 102 are coplanar. The arrangement of the needle pairs 102 around the longitudinal axis A is star-shaped, the radial distribution of the needle pairs 102 around the longitudinal axis being substantially even.

The device 101 further comprises two frames 110 having a central opening 111, one frame embracing the first needles 103a of each pair and the other frame embracing the second needles 103b of each pair. The first and second needles of each pair are embraced at the central sections 106 of their shafts. The frames 110 are ring-shaped and form a closed loop. They comprise two half-circle shaped frame members 111 and 112 which are connected by a hinge at one end 113 and detachably connected at the other end 114. The frames 110 and the needles 103 may be slidable with respect to each other in the longitudinal direction.

There is further provided for a tissue-collar manipulating device 120, the tissue-collar manipulating device comprising a support 121 and a disc shaped head 122 having indentations 123 at regular intervals along its circumference. The tissue-collar manipulating device serves to define and freeze an even radial distribution of the needles inside the opening.

The device allows for a plurality of sutures to be regularly, precisely and quickly distributed over the circumference of two separate pieces of hollow, strand-shaped tissue having small diameter, such as a blood vessels, to connect the pieces. It is suitable for use in microsurgery and automated surgery.

Upon application of the device, in a first step as shown in FIG. 16, the surgeon axially aligns the device with two separate loose ends 131 and 132 of a blood vessel to be connected. The device is in its ground state having one frame 110 attached to the first needles 103a of each pair of needles and the other frame 110 embracing the second needles 103b of each pair needles. The needle pairs are evenly distributed. One tip end of the device is then inserted into the hollow interior of the loose end of at least one blood vessel.

Once the tip end of the device is inside the hollow interior of the loose end of the vessel, the head 122 of the tissue-collar manipulating device 120 is inserted into the space between the respective needles 103 of each pair and operated to maintain an even distribution of the needles. This is shown in FIG. 17. The respective needles 103 are then slid relative to the frame ring 110 in a direction towards the vessel, the needle tips thereby progressing further away from the longitudinal axis and puncturing the wall of the blood vessel 131 from the inside. The needles may be slid relative to the frame ring all at once or one by one. The tissue-collar manipulating device 120 may also be operated to evenly distribute the needles before the tip end of the device is inserted into the blood vessel. Also, both tip ends of the device may be inserted to both loose ends of the vessel before the needles are evenly distributed and/or before the needles may be slid relative to the frame ring.

As shown in FIGS. 18 and 19, the frame 110 is then removed from the device before the stitches are formed in a well-known way upon completing movement of both the needles through the wall of the vessel and knotting together the ends of the suture connecting the two needles of a pair. As shown in FIG. 18, the tissue-collar manipulating device 120 may be held in place for some time to guide the movement of the needles.

The fact that all needles and the vessel are held in place relative to each other during the formation of each of the stitches allows for a more precise outcome of the procedure.

The device shown in FIGS. 20 to 24 is also generally designated with numeral 101 and comprises a plurality of pairs of identical needles 103. Identical entities to the device of FIGS. 16 to 19 are labelled with the same reference signs and only differences to the device shown in FIGS. 16 to 19 will be discussed in the following.

The frame members 110 of the bracket are configured as two separate rings 140 and 141 which are spaced apart from one another in longitudinal direction. All rings are arranged about the common longitudinal axis Z and are essentially identical. The two rings 140 and 141 of the frame member may be connected to one another but may alternatively only be associated by way of the needles.

The frame members 110, specifically the proximal rings 140 thereof, are connected to one another by means of the connecting stick 145, which extends in the direction of the longitudinal axis Z. The connecting stick may be formed two separate pieces 146 and 147, which are releasably connected at an interface 148, for example, by mechanical fastening. Both pieces 146 and 147 may be identical and the connecting stick 145 is circular in diameter. The connecting stick 145 sets a configuration of the device 101 where the frame members 110 and all rings 140 and 141 thereof are arranged symmetrically about the common longitudinal axis Z. The connecting stick is not connected to either of the needles or the sutures.

The device further comprises two positioning sticks 150 and 160 which are arranged in the common longitudinal axis Z. The distal end 151 of the first positioning stick 150 longitudinally projects beyond the tips 107 of the first needles 103a and the distal end 161 of a second positioning stick 160 longitudinally projects beyond the tips 107 of the second needles 103b.

The positioning sticks 150 and 160 have a circular cross-section corresponding to the circular shape of the interior of the vessel to be sutured. The distal ends 151 and 161 of the positioning sticks 150 and 160 are tapered for easier insertion to the interior of the loose ends 131 and 132 of the vessel.

The positioning sticks 150 and 160 are mounted to the frame members 110, specifically to the distal rings 141 thereof, at their proximal ends 152 and 162. At the proximal ends 152 and 162 of the positioning sticks, the positioning sticks or the distal rings 141 of the frame members 110 or the proximal ends 152 or 162 of the positioning sticks 150 or 160 may comprise an annular chamfer 152a and 162a, which, upon inserting the distal ends 151 and 161 of the positioning sticks 150 and 160 into the vessels 131 and 132, facilitates the formation of a flange 131a and 132a at the vessel wall in immediate proximity to its loose end. The needles 103 are, for example, contained in the device 101 such that the needle tips 107, upon moving the needles 103 in a distal position, exit the distal rings where the annular chamfer 152a or 162a, respectively, is located and are guided to pass the annular chamfer 152a or 162a, respectively. This way, the needles can pierce the vessel wall at the flange 131a or 132a, respectively, close to its loose end, which supports the formation of a clean stitch.

When using the device 101 of this embodiment, the distal end 151 of the first positioning stick 150 is inserted to the interior of one loose end 131 of the vessel to be sutured, and the distal end 161 of the first positioning stick 160 is inserted to the interior of the other loose end 132 of the vessel to be sutured. By inserting the distal ends 151 and 161 of the positioning sticks 150 and 160 into the vessels, a correct positioning of the device 101 and thus of the needles 103 relative to the loose ends 131 and 132 of the vessel can be facilitated before the suturing is started.

The process is the continued in a manner as described in connection with FIGS. 16 to 19. Different stages are shown in FIGS. 20 to 24. Like the frame rings also the positioning sticks 150 and 160 are removed from the device at the end of the procedure and before the stitches are finalized. In this regard, the frame rings may be opened and the two separate pieces 146 and 147 of the connecting stick 145 may be separated at the interface 148. Each half of the device including one piece of the connecting stick, one pair of frame rings and one positioning stick is then moved backwards in an axial direction (illustrated by arrow A in FIG. 23) to pull the positioning stick out of the vessel and subsequently removed from the vessel ends and the incomplete sutures. Finally, the stitches are formed.

FIG. 25 shows another embodiment of a device according to the invention. Identical entities to the device of FIGS. 20 to 24 are labelled with the same reference signs and only differences to the device shown in FIGS. 20 to 24 are now discussed. Specifically, the device shown in FIG. 25 differs over the device shown in FIGS. 20 to 24 in that the two pieces 146 and 147 are not engaged to one another to form a connecting stick, but are separate from one another during application. This way, a proper fitting of each half of the device can be made to each of the loose ends of the vessel, regardless of the relative position of the two loose ends. Upon application, once the distal ends 151 and 161 of the positioning sticks 150 and 160 of this embodiment have been inserted to the vessel ends, the two pieces 146 and 147 may be connected to form a connecting stick and result in the embodiment of FIGS. 20 to 24.

Referring to FIG. 26, the tissue connector device 1010 is in the form of a surgical needle comprising an arc-shaped main portion 1011 of the shaft. One end portion of the main portion 1011 is provided with a bore 1012 for attaching a suture thread 1100, which is made of a material which is physiologically compatible. The material of the suture thread 1100 may be absorbable by the body of the patient.

The bore 1012 are provided with a hole 1013 in the main portion 1011 of the shaft. In order to fix the suture thread to the main portion 1011 of the shaft, the bore 1013 may be closed about the suture end by swaging, squeezing or any other process which is suitable to fix the suture thread 1100 with the main portion 1011 of the shaft.

The other end of the main portion 1011 of the shaft is connected with the tip portion 1020 of the shaft, which is arc-shaped as well. The radius of the curvature of the tip portion 1020 of the shaft is smaller than that of the curvature of the main portion 1011 of the shaft. The tip portion 1020 of the shaft and the main portion 1011 of the shaft are portions of a one-piece metal part. For example, shaft may be made of stainless steel or any other suitable material.

The tip portion 1020 of the shaft comprises the tip 1030 of the needle 1010. The distal end of the tip portion 1020 of the shaft (which is not adjacent the main portion 1011 of the shaft) is formed by the tip 1030 of the needle 1010.

As shown in FIG. 26, the angle between the tip 1030, i.e. between the direction into which the tip is directed (or the longitudinal axis of the tip 1030) and the longitudinal axis of part 1011' of the main portion 1011 of the shaft which is adjacent to the tip portion 1020 of the shaft is denominated with α. The angle α may be in the range of, e.g., approximately 45° to 90°. Accordingly, the tip 1030 of the needle is not directed along the longitudinal axis L of the portion 1011" of main portion 1011 of the shaft which is adjacent the tip portion 1020 of the shaft but bent backwards as shown in FIG. 26. Thus the tip 1030 of the needle 1010 is directed backwards with respect to the main portion 1011 of the shaft of the needle 1010. The leading edge 1040 of the needle 1010 is not necessarily an acute tip, but a rounded portion.

In order to puncture the needle 1010 into the tissue the needle is inserted into the vessel, nerve etc. and then moved backwards so that the tip penetrates the wall of the vessel or nerve. Thereafter the surgeon pulls or pushes the needle through the penetration together with the suture thread 1100 in order to suture the open ends of the vessels etc. with each other.

FIG. 27 shows an embodiment which is identical to the embodiment of FIG. 26 except the grip portion 1050. This portion extends beyond the bore for fixing the suture and serves as a grip or for mounting a grip for a better handling of the needle.

The embodiment of FIG. 28 is directed to a system of two needles 1010 which are linked to each other by a common suture thread 1100. The needles 1010 are identical and each correspond to the needle which is shown in FIG. 26. The embodiment of FIG. 29 shows a system of two needles 1010 which are linked to each other by a common suture thread 1100 as well as by a linking portion 1200. The portion 1200 may be removed from the needles 1010 by braking. In FIG. 23 the two needles 1010 are located opposite of the linking portion 1200 and are arranged symmetrically in relation to the linking portion 1200. The system of FIG. 28 or 29 may be used by the surgeon by inserting each of the two needles 1010 into an open end portion of a vessel or the like. Thereafter the tips 1030 of the needles 1010 penetrate the respective walls of the vessels or the sheaths of nerves etc., the needles are pulled or pushed through the penetrations, the suture is cut off the needles and the ends of the suture are connected with each other.

To summarize, the device as presented herein may allow for a plurality of sutures to be regularly, precisely and quickly applied to a very small piece of tissue such as small nerves, vessels or a cornea. It may also aid to hold the tissue in place and may be used without separate clamps to hold the tissue in place.

In one embodiment, the device may allow for a plurality of sutures to be regularly, precisely and quickly distributed over the circumference of two separate pieces of hollow, strand-shaped tissue having small diameter, such as a blood vessels, to connect the pieces.

The device may be suitable for use in microsurgery and automated surgery.

Aided by an angled orientation of the tip in relation to the curvature of the main shaft, in one embodiment, the tip of the tissue connector device may be inserted into the vessel or under the sheath of a nerve and can be punctured through the wall of the vessel or through said sheath of a nerve by a backward movement with relation to the direction of the insertion of the needle so that the tip penetrates the wall or the sheath. The angled orientation of the tip may allow to reliably suturing vessels or nerves having very small inner diameters with each other while minimizing the risk that opposite walls are sutured to each other. The tissue connector device may allow a manual as well as an automated preparation of a suture.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

Unless otherwise stated, the use of the expression "and/or" between the last two members of a list of options for selection indicates that a selection of one or more of the listed options is appropriate and may be made.

It should be understood that where the claims or specification refer to "a" or "an" element, such reference is not to be construed as there being only one of that element.

While this disclosure has been described in terms of certain embodiments and generally associated methods, alterations and permutations of the embodiments and methods will be apparent to those skilled in the art. The disclosure is to be understood as not limited by the specific embodiments described herein.

The invention claimed is:

1. A surgical device for suturing human or animal tissue, the device comprising a bracket and two or more pairs of surgical needles,
   the bracket being configured to detachably receive said two or more pairs of surgical needles,
   each pair comprising a first needle and a second needle connected by a suture thread, the first and second needles of each pair extending in opposite directions, and the two or more pairs of needles being arranged radially around and extend along a common longitudinal axis,
   each of the needles comprises a needle body comprising a curved main shaft portion connected to or connectable with the suture thread, and a needle tip portion integral with the curved main shaft, the needle tip portion comprising a curved portion and the needle tip such that the needle tip portion is hook-shaped, curved inwardly and bent backwards with respect to the main shaft portion, a radius of curvature of the curved portion of the needle tip portion being smaller than a radius of curvature of the main shaft portion,
   the needle being made of one-piece metal part,
   wherein the bracket comprises at least two frame members, one of the at least two frame members embracing the first needles and the other one of the at least two frame members embracing the second needles,
   wherein the curved main shaft of the needles has a central section, such that the frame members embrace the needles at said central section, and
   wherein each of the frame members has a central opening with the needle tip portions pointing towards the central opening.

2. The device of claim 1, wherein the angle between the needle tip and said main shaft portion ranges from 30° to 110°.

3. The device of claim 1, wherein the angle between the needle tip and said main shaft portion ranges from 45° to 90°.

4. The device of claim 1, wherein the needles of each pair of needles are connected by said suture thread, connecting respective proximal ends of the needles in said pair of needles.

5. The device of claim 1, wherein the needles are evenly radially distributed around the longitudinal axis.

6. The device of claim 1, wherein the at least two frame members are arranged along said common longitudinal axis.

7. The device of claim 6, wherein the at least two frame members are slidably displaceable along the common longitudinal axis.

8. The device of claim 1, wherein each of the at least two frame members is composed of two or more frame portions, detachably connected one to the other.

9. The device of claim 1, wherein each of the frame members is configured for simultaneous displacement of the needles held by the respective frame member into the tissue to simultaneously pierce the tissue.

10. The device of claim 1, wherein the tissue is a tubular organ, and each of the frame members is associated with a positioning stick at a distal end of the frame members, configured to be inserted into the tubular organ.

11. The device of claim 10, comprises an annular chamfer at the distal end of the frame member or at the proximal end of the positioning stick, configured guide the needles' tips to pierce the loose end of the tissue when the needles are distally displaced.

12. The device of claim 1, configured for suturing two loose ends of a tubular organ.

13. A surgical device for suturing human or animal tissue, the device comprising a bracket and two or more pairs of surgical needles,
   the bracket being configured to detachably receive said two or more pairs of surgical needles,
   each pair comprising a first needle and a second needle connected by a suture thread, the first and second needles of each pair extending in opposite directions, and the two or more pairs of needles being arranged radially around and extend along a common longitudinal axis,
   each of the needles comprises a needle body comprising a curved main shaft portion connected to or connectable with the suture thread, and a needle tip portion integral with the curved main shaft,
   the bracket comprises at least two frame members, one of the at least two frame members embracing the first needles and the other one of the at least two frame members embracing the second needles, and the curved main shaft of the needles having a central section, such that the frame members embrace the needles at said central section, and each of the frame members has a central opening, with the needle tip portions pointing towards the central opening.

* * * * *